United States Patent
Mahiou et al.

[11] Patent Number: 5,990,284
[45] Date of Patent: Nov. 23, 1999

[54] PROCESS FOR THE ISOLATION AND PURIFICATION OF ZEAMATIN

[75] Inventors: Belaid Mahiou; Robert Rieger, both of Westminster, Colo.

[73] Assignee: Univera Pharmaceuticals, Inc., Broomfield, Colo.

[21] Appl. No.: 09/146,805

[22] Filed: Sep. 4, 1998

Related U.S. Application Data

[60] Provisional application No. 60/057,530, Sep. 4, 1997.

[51] Int. Cl.$^6$ .............................. C07K 1/00; C07K 14/00; A23J 1/00

[52] U.S. Cl. ...................... 530/376; 530/350; 530/370; 530/412; 530/414; 530/416; 530/417; 530/418; 530/422; 530/427

[58] Field of Search .................................. 530/376, 350, 530/370, 412, 414, 416, 417, 418, 422, 427

[56] References Cited

U.S. PATENT DOCUMENTS

| | | | |
|---|---|---|---|
| 5,521,153 | 5/1996 | Roberts et al. | 514/2 |
| 5,559,034 | 9/1996 | Roberts et al. | 435/320.1 |

OTHER PUBLICATIONS

Paulis et al, *Chemical Abstract*, 1 vol. 109, p. 520, Ref. # 36789X, 1988 (Cereal Chem. vol. 65, No. 3, pp. 215–222).
Sofer et al, *Biotechniques*, vol. 1, No. 4, pp. 198–203, 1983.
Bonnerjea et al, *Bio/Technology*, vol. 5, pp. 955–958, 1986.
Bartlett and Smith (1991) Clinical Microbiology Reviews 4:137–149.
Bodey et al. (1992) Eur. J. Clin. Microbiol. Infect. Dis. 11:99–109.
Cox and Perfect (1993) Curr. Opin. Infect. Dis. 6:422–426.
Fox (1993) ASM News 59:515–518.
Kujath (1992) Mycoses 35:225–228.
Nouza (1992) Infection 20:113–117.
Roberts and Selitrennikoff (1990) J. Gen. Microbiol. 136:1771–1778.
Samonis and Bafaloukos (1992) in vivo 6:183–194.
Sternberg (1994) Science 266:1632–1634.
Vigers et al. (1992) Plant Science 83:155–161.
Vigers et al. (1991) Molecular Plant–Microbe Interactions 4:315–323.

*Primary Examiner*—Cecilia J. Tsang
*Assistant Examiner*—Abdel A. Mohamed
*Attorney, Agent, or Firm*—Swanson & Bratschun LLC

[57] ABSTRACT

Methods are herein provided for the isolation and purification of zeamatin, an antifungal protein from corn. The subject methods use capture chromatography and reverse phase chromatography. The methods herein described is superior to prior art techniques as it the eliminates ammonium sulfate precipitation and centrifugation steps.

19 Claims, 4 Drawing Sheets

PROCESS FOR THE ISOLATION AND PURIFICATION OF ZEAMATIN

RELATED APPLICATIONS

This application claims priority from U.S. Provisional Patent Application Ser. No. 60/057,530 filed Sep. 4, 1997, entitled "Process for Isolation and Purification of Zeamatin."

FIELD OF THE INVENTION

The present invention relates generally to a novel process for the isolation and rapid purification of the antifungal protein zeamatin from corn.

BACKGROUND OF THE INVENTION

Systemic fungal infections have become an increasing problem over the last three decades (see, e.g., Bartlett (1991) Clin. Microbiol. Rev. 4:137–149; Bodey et al. (1992) Eur. J. Clin. Microbiol. Infect. Dis. 11:99–109; Sternberg (1994) Science 266:1632–1634; Cox (1993) Curr. Opin. Infect. Dis. 6:422–426; Fox (1993) ASM News 59:515–518; Kujath (1992) Mycoses 35:225–228; Samonis and Bafaloukos (1992) In Vivo 6:83–194, Nouza (1992) Infection 20:113–117). The most serious infections occur in the immunocompromised host and can result in disseminated systemic mycoses (see, e.g., Bartlett (1991) Clin. Microbiol. Rev. 4:137–149; Bodey et al. (1992) Eur. J. Clin. Microbiol. Infect. Dis. 11:99–109; Sternberg (1994) Science 266:1632–1634; Cox (1993) Curr. Opin. Infect. Dis. 6:422–426; Fox (1993) ASM News 59:515–518; Kujath (1992) Mycoses 35:225–228; Samonis and Bafaloukos (1992) In Vivo 6:83–194,Nouza (1992) Infection 20:113–117).

Current treatment for systemic fungal infections is primarily limited to two groups of drugs: the polyene macrolide antibiotics, such as Amphotericin B and nystatin; and the imidazoles, such as ketaconazole and miconazole. Toxicity and resistance to the drugs in use necessitates the discovery and development of new antifungal products.

Zeamatin, a plant protein isolated from corn, has been demonstrated to have antifungal activity in vitro against numerous human pathogens including *Candida albicans*. (See, Roberts and Selitrennikoff (1990) J. Gen. Microbiol. 136:1771–1778; Roberts el al. U.S. Pat. No. 5,521,153, issued May 28, 1996; Vigers and Selitrennikoff (1991) Mol. Plant Microbe Interac. 4:315–323; Vigers et al. (1992) Plant Sci. 83:155–161). It has been reported that zeamatin, a permatin, acts to inhibit fungi by permeabilizing the plasma membrane, causing the release of the contents of the cell (Roberts and Selitrennikoff (1990) J. Gen. Microbiol. 136:1771–1778).

In addition to its own antifungal activity, zeamatin acts synergistically with a number of antifungal compounds including clotrimazole, Amphotericin B, ketoconazole, grisefulvin, nystatin and nikkomycin X and Z. (See, Roberts and Selitrennikoff (1990) J. Gen. Microbiol. 136:1771–778; Roberts et al. U.S. Pat. No. 5,521,153, issued May 28, 1996; Vigers and Selitrennikoff (1991) Mol. Plant Microbe Interac. 4:315–323). For example, zeamatin enhances the antifungal activity of nikkomycin X and Z against Candida between 100–1000 fold, and can enhance the activity of Amphotericin B against yeast by approximately 3 fold.

Due to its antifungal activity and its synergistic effect on certain antifungal agents, zeamatin may be a useful agent in the treatment of systemic fungal infections. In particular, co-administering zeamatin with other antifungal agents may permit the use of smaller doses of the antifungal agent, thereby reducing the potential for toxic side effects of those agents.

Given the potential for the use of zeamatin, it is desirable to have a high-yield procedure for isolating and purifying the protein on a large scale. The reported method for isolating and purifying zeamatin, illustrated in FIG. 1, uses an ammonium sulfate precipitation step, followed by centrifugation and diafiltration, to obtain a crude protein fraction. This fraction is then further purified by ion-exchange chromatography on CARBOXYMETHYL-SEPHADEX™, a cation exchange dextran resin which can be purchased from Sigma Chemical Company or Pharmacia Biotech. The proteins are eluted from the column in a salt gradient, and fractions containing zeamatin activity are pooled. The pooled fractions are subjected to diafiltration using a 10 kDa nominal-molecular-weight cutoff filter, then subjected to reverse phase chromatography using a C-18 resin. Prior art methods for zeamatin purification are described in U.S. Pat. Nos. 5,521,153 and 5,559,034, each of which is specifically incorporated herein by reference in their entirety. These methods are performed on a small scale and are not amenable to scale-up.

The object of the instant invention is to provide a simple, rapid and efficient method for the purification of zeamatin that does not require the time-consuming ammonium sulfate precipitation and centrifugation steps and is amenable to scale-up. Another object of the present invention is to identify column conditions that allow the use of high water content eluents.

SUMMARY OF THE INVENTION

The present invention includes a process for isolating and purifying zeamatin, an antifungal protein isolated from corn. In one embodiment of the present invention, the method comprises: extracting ground corn with an aqueous buffer to yield an initial suspension; filtering said initial suspension to yield a filtrate; fractionating said filtrate using capture chromatography, and collecting one or more initial eluted fractions containing zeamatin; further fractionating said initial fractions containing zeamatin using reverse phase chromatography and collecting one or more further eluted fractions containing zeamatin.

The present invention provides a commercially viable process for the rapid and efficient purification of zeamatin having desirable physiological activity.

DETAILED DESCRIPTION OF THE PREFERRED EMBODIMENTS

The present invention includes a novel process for the isolation and purification of zeamatin, an antifungal protein isolated from corn. In one embodiment of the present invention, the process comprises: extracting ground corn with an aqueous buffer to yield an initial suspension; filtering said initial suspension to yield a filtrate; fractionating said filtrate using capture chromatography, and collecting one or more initial eluted fractions containing zeamatin; further fractionating said initial fractions containing zeamatin using reverse phase chromatography, and collecting one or more further eluted fractions containing zeamatin.

The present invention provides a commercially viable process for the rapid and efficient purification of zeamatin having desirable physiological activity.

Figure 2:
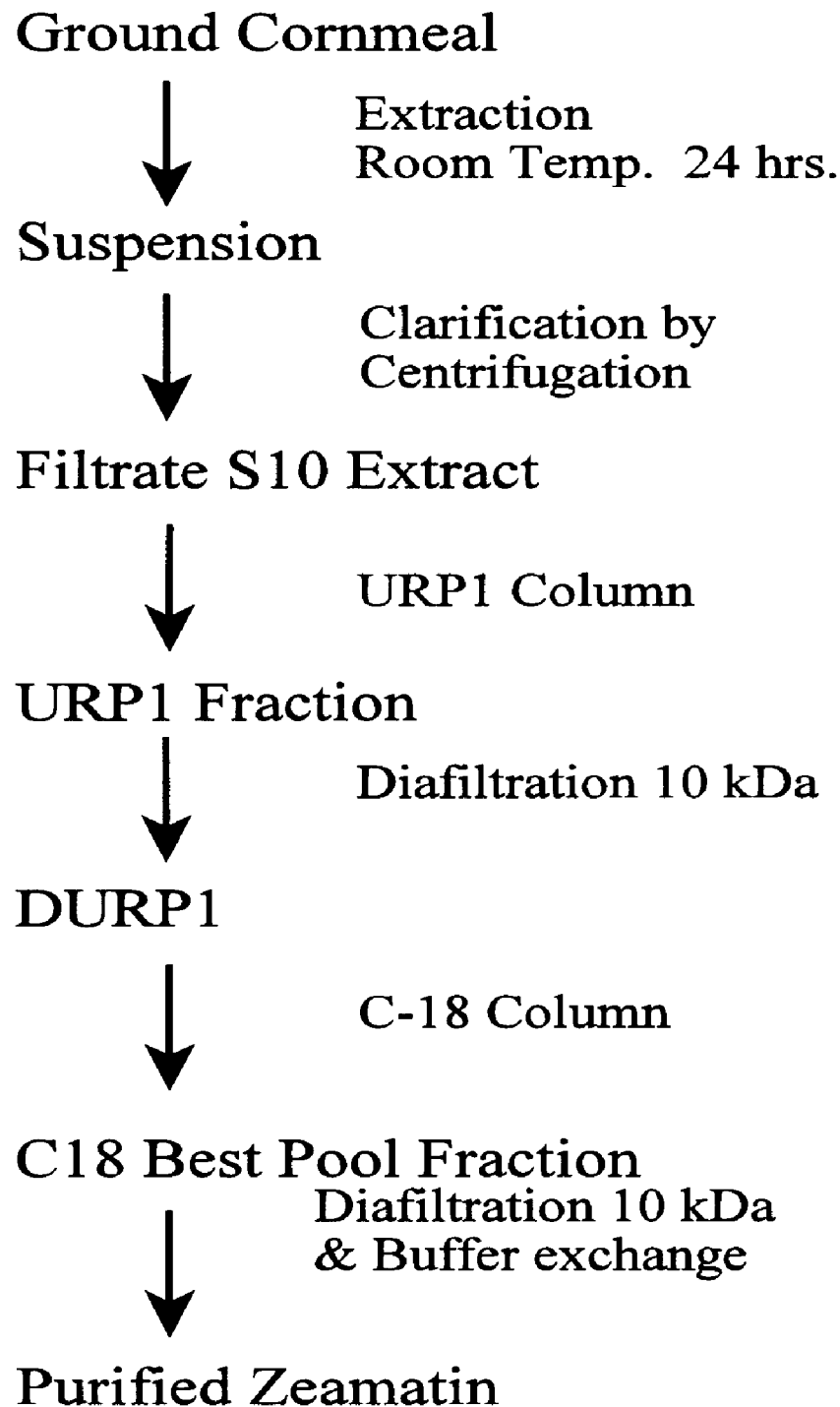
FIG. 2 illustrates schematically the method of the instant invention.

In a preferred embodiment of the invention, illustrated schematically in FIG. 2, high lysine cornmeal is milled to an appropriate size and extracted in an aqueous buffer. The resulting suspension is then clarified by filtration. In a preferred embodiment, the filtration is achieved using an initial pressure filtration through filter paper, followed by a second pressure filtration through a glass fiber filter.

Several extraction parameters were investigated to obtain insight into the parameters that affect the extraction and require optimization. Among the parameters investigated were: particle size of the cornmeal, extraction time, extraction temperature, ratio of biomass to extraction fluid and pH of the extraction fluid. The efficiency of the extraction was measured by the amount of total protein in the clarified extract and its antifungal activity. This investigation revealed that of the parameters studied only particle size of the cornmeal and extraction time affected the amount of zeamatin in the extract. Although temperature did not affect the amount of zeamatin extracted, it was increased from 4° C. to room temperature to ease of manufacture on a large scale. The extraction time was increased from 2 to 24 hours and the cornmeal was milled further to pass a 220 $\mu$m screen. Further particle size reduction would have resulted in a clarified extract (S10) of high solid content, which would have negatively impacted the URP1 column.

Clarification of the extract was achieved by filtration using filters of various porosity. The best results are obtained using 40 $\mu$m filter paper. Filtration yielded a better quality of clarified extract than centrifugation. The quality of the S10 extract was assessed by ultraviolet-visible spectroscopy. The S10 clarified extract obtained by filtration had higher activity and exhibited a lower absorbance over a wide range of wavelengths (220 and 600 nm), which is indicative of lower dissolved solids in the S10 extract. When 8 $\mu$m filter paper was used, an average filtration rate of 1.2 L/min/m$^2$ was achieved at moderate pressure. In a number of batches, the filtration pressure reached 40 psi. This is not unexpected, as the filtration feed exhibits high amounts of both dissolved and non-dissolved solids (density 1.07 kg/L). The dissolved solids tend to clog the filter and the non-dissolved solids form a compressible cake. The average cake height (thickness) observed in the batches performed was 7 cm, thus, at higher pressure, liquid flow through the cake was completely suppressed. A similar filtration rate and much lower pressure was observed when the porosity of the filter paper was increased to 40 $\mu$m (average filtration rate 1.1 L/min/m$^2$ and maximum pressure below 20 psi). Only about 69% of the extraction buffer used in the extraction is recovered after filtration. The filtrate is usually stored at −70° C. to inhibit any biological growth until further processing.

Figure 1:
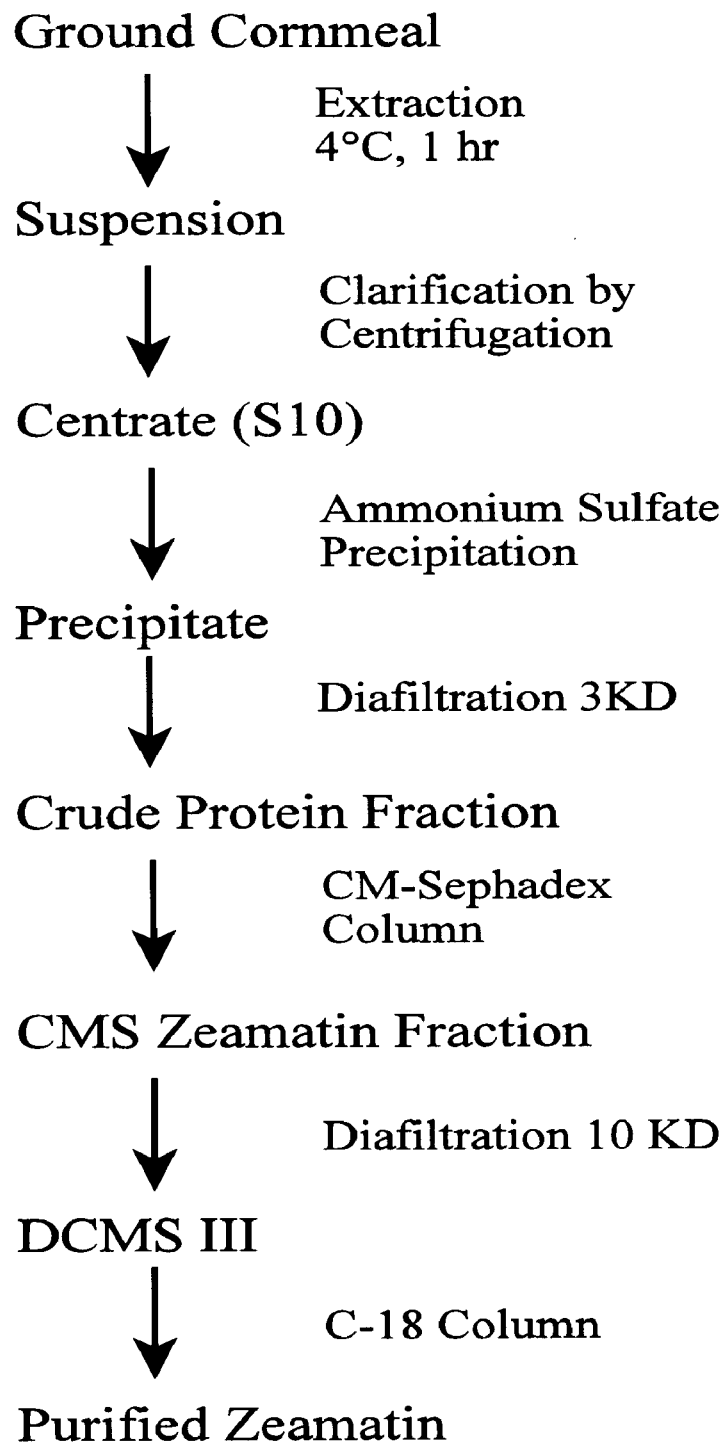
FIG. 1 illustrates schematically the prior art procedure for purification of zeamatin from corn.

After filtration the S10 extract is transferred to a capture column (referred to herein as "URP1 column"). The URP1 column provides a beneficial alternative to the use of the ammonium sulfate precipitation and CM-SEPHADEX™ (Pharmacia Biotech) column chromatography steps currently used to purify proteins (FIG. 1). Partitioning of proteins by ammonium sulfate precipitation requires a centrifugation step to collect the precipitated proteins. Due to the size of the protein of interest, the selection of the appropriate centrifuge and the operation of such equipment in a production plant will likely be cost prohibitive. The present method does not include a centrifugation step.

The use of CM-SEPHADEX™ (CMS) columns creates a number of problems on a large scale, which can be overcome by the use of a URP1 column. First, the resin bed volume of these columns expands as the ionic strength of the mobile phase decreases (lower concentrations of NaCl) and decreases with increasing ionic strength of the mobile phase. These changes in resin bed-volume are accompanied with changes in linear velocity and pressure drops across the resin bed. Additionally, the failure of all the zeamatin to elute in a single fraction on a CM-SEPHADEX™ column using a linear gradient adversely affects the purity of the product obtained. Using a linear gradient and linear velocity, which is preferred for large scale purification, zeamatin elutes in two fractions, one of which has a much lower purity. The purity of zeamatin in the dialyzed best pool obtained from the CMS-SEPHADEX™ column was only enhanced by 6.7 fold. On the URP1 resin zeamatin elutes in one single fraction and the purity increased from 1.4% in the clarified extract to 40–45% in the URP1 best pool. In this single step, the purity of zeamatin was increased by an average factor of 30 times without affecting the recovery. The loading capacity of the CMS-SEPHADEX™ resin is much lower than that of URP1 resin. This dramatically impacts the size that can be used for a production column, and thus the cost of manufacture. Despite the high protein and carbohydrate content in the clarified extract, URP1 resin has a high loading capacity. This allows for a reduction of the size of the column required. Finally, the cost of the URP1 resin is much lower than that of CMS.

The URP1 column resin is an aromatic resin, selected from but not limited to the group consisting of CG 161, CG 71 and CG 3000, each of which is available from Toso Haas in Tokyo, Japan. In a preferred embodiment the URP1 resin is AMBERCHROM™ MD-P CG 161 SD (Toso Haas), which has a 35 $\mu$m particle size. The resin can be used 10–20 times before cleaning without resin fouling.

Following loading of the URP1 column, zeamatin is eluted using a gradient of organic solvent. In a preferred embodiment, the zeamatin is eluted using a two step gradient of acetonitrile in 0.1% acetic acid, and zeamatin is eluted in 35% acetonitrile/0.1% acetic acid. The presence of the zeamatin in the collected fractions can be verified through a number of procedures known in the art, including, but not limited to, high pressure liquid chromatography (HPLC), sodium dodecyl sulfate polyacrylamide gel electrophoresis (SDS-PAGE), and assays for zeamatin antifungal activity, as described in Example 3.

In one embodiment the eluted zeamatin is concentrated by first removing the organic solvent, preferably through the use of reduced pressure and gentle heating. The resulting aqueous solution is then lyophilized and redissolved in aqueous solvent. In a preferred embodiment the URP1 fraction is concentrated and then dialyzed using a Tangential Flow Filter (TFF) system equipped with a 0.5 m$^2$ regenerated cellulose membrane with a nominal molecular weight cut-off (NMWCO) of 5 kDa. A relatively low loss of zeamatin (less than 10%) is observed using a 5 kDa membrane. It is believed that the loss is incurred during the dialysis of the concentrate to exchange the buffer to 20 mM sodium chloride. The concentrated and dialyzed aqueous zeamatin solution is then stored at −70° C. until further processing.

The concentrated zeamatin from the URP1 column is then optionally filtered, preferably through a 0.45 µm filter and dissolved in aqueous medium. In some embodiments, an optional cation exchange chromatography step is then performed. This optional step increases the purity of the zeamatin, which in turn increases the loading capacity of the subsequent reverse phase column. By increasing the loading capacity of the reverse phase column, it is possible to use smaller, and hence cheaper, reverse phase columns. The preferred cation exchange resin for this optional step is a carboxymethyl cation exchange resin, such as CM 650 (Toso Haas). Following application of the zeamatin, an aqueous salt solution is applied to elute zeamatin from the column. Again, the presence of zeamatin in the eluted fractions can be assayed by the methods described above for assaying fractions from the first column.

The zeamatin from the URP1 column (or from the optional cation exchange column), is dissolved in aqueous solvent and further fractionated on a reverse phase column. The preferred column medium is a C-18 resin having a hydrophilic end cap. Several potential C-18 resins from various vendors were investigated in order to select the preferred resins for this final purification step. The majority of the resins tested did not respond well to the elution solvent. The common problem was loss of resolution and loading capacity after 4 or 5 runs. The cause of this problem resides in the type of end cap. The resins that failed are manufactured with the conventional C-1 end cap that gives a totally hydrophobic support surface. When the mobile phase composition is primarily water, the C-18 ligands fold and form a compact mat to escape the water, which leaves a small surface for interaction with analytes in the samples loaded resulting in lower loading capacity and poor resolution. In a preferred embodiment, therefore, a C-18 resin with a hydrophilic end cap is used. In the most preferred embodiment the C-18 resin used is URP-13™ (15 µm particle size and 200 Å pore size, purchased from YMC, Inc.). URP-13™ is preferred because of its high loading capacity, its ability to be used with solvents containing high levels of water, and its high resolving activity.

Zeamatin is eluted from the C-18 column using a gradient of organic solvent in aqueous trifluoroacetic acid (TFA). In preferred embodiments, the organic solvent is acetonitrile, and zeamatin is eluted in 37% acetonitrile. The presence of zeamatin in the eluted fraction(s) can be determined by the methods described above.

The zeamatin eluted from the reverse phase column can be concentrated by any of the many methods known in the art for protein concentration. For example, the zeamatin (in acetonitrile) can be concentrated using a rotary evaporator, dialyzed against a salt solution using a 5 kDa nominal molecular weight cutoff filter, and then lyophilized. Alternatively, the zeamatin may be concentrated using a diafiltration system. The use of a diafiltration system may prevent protein denaturation and degradation, and also allows for solvent and buffer exchange.

Example 1 describes the isolation and purification of zeamatin from ground cornmeal on a 1 kg scale and Example 2 describes the isolation and purification of zeamatin from ground cornmeal on a 5 kg scale.

Example 3 describes the various methods used to analyze the various samples for the presence and purity of zeamatin. (See, Roberts and Selitrennikoff (1990) J. Gen. Microbiol. 136:1771–1778, which is incorporated herein by reference in its entirety). Using the prior art method (FIG. 1) the S10 extract is purified 3.6 fold by ammonium sulfate precipitation and 20 fold by CM-SEPHADEX™ chromatography. Zeamatin purified to homology (50 fold) is obtained by further fractionation through a Phenyl Sepharose column, yielding 1 mg of zeamatin per 100 g of corn seeds (Roberts and Selitrennikoff (1990) J. Gen. Microbiol. 136:1771–1778). Purification by HPLC elution, results in zeamatin purified 68 fold and higher (Roberts and Selitrennikoff (1990) J. Gen. Microbiol. 136:1771–1778).

Figure 3:
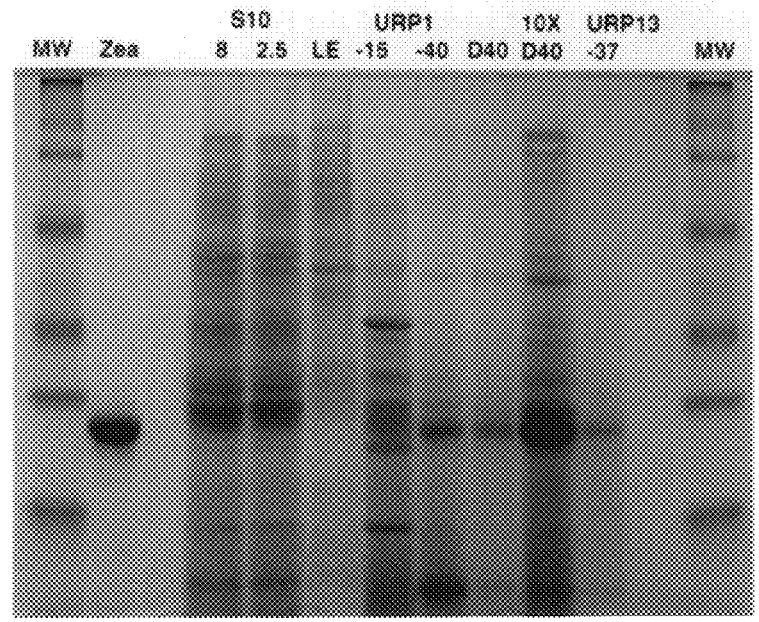
FIG. 3 shows the results of an SDS-PAGE analysis of the products obtained using the prior art method (Lane 2) and the method of this invention: S10 fractions (Lanes 3–5), URP1 fractions (Lanes 6–9) and C-18 fraction (Lane 10).

In order to obtain reliable estimates of the purity of the product obtained from each step, in addition to antifungal activity assays, purity was also determined by densitometry of silver-stained or Coomassie stained proteins separated by SDS-PAGE (FIG. 3). The S10 extract was purified approximately 30 fold by URP1 chromatography. Purities of up to 98% were observed following the C-18 reverse phase chromatography, providing 200 mg of zeamatin from 5 kg of cornmeal.

Figure 4:
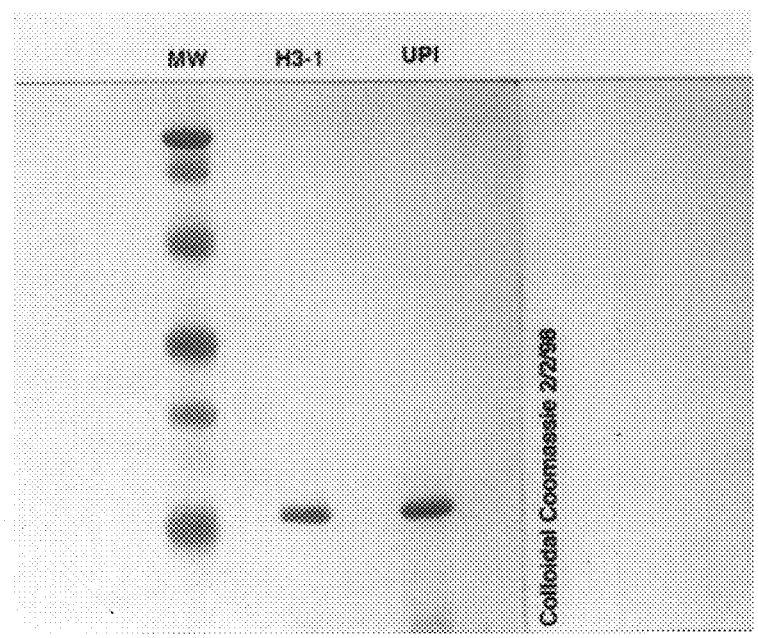
FIG. 4 shows the results of an SDS-PAGE analysis of the product obtained using the prior art method (Lane 2) and the method of this invention (Lane 3).
Figure 5:
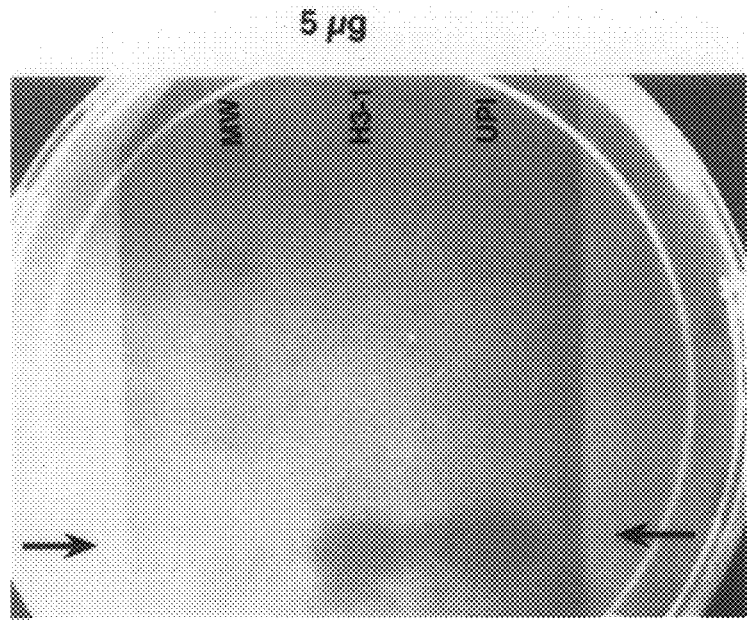
FIG. 5 shows the results of bioautography of the product obtained using the prior art method (Lane 2) and the method of this invention (Lane 3).
Figure 6:
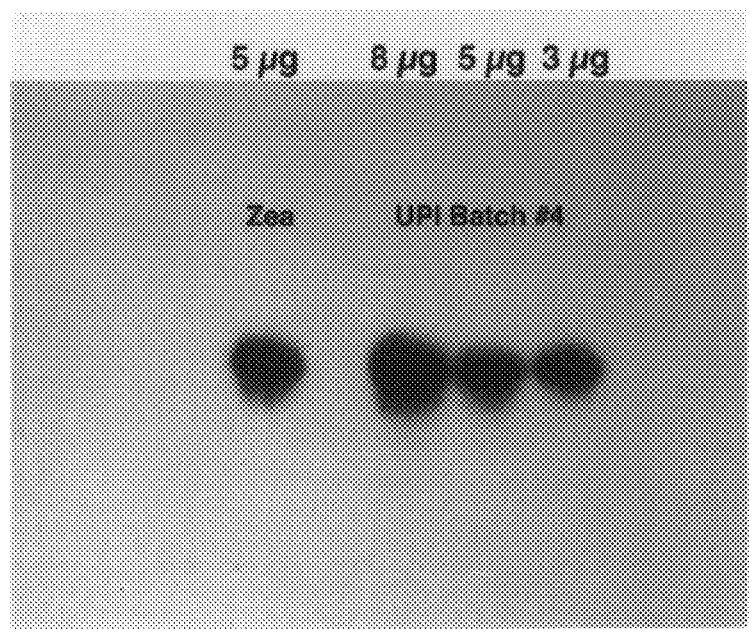
FIG. 6 shows the results of a western blot analysis of the product obtained using the prior art method (Lane 1) and the method of this invention (Lanes 2–4).

FIG. 3 shows the results of Coomassie stained proteins separated by SDS-PAGE for each step of the method of the present invention compared to the prior art method. Lanes 1 and 11 are a molecular weight standard, Lane 2 (Zea) is the final product obtained from the prior art method of purification, Lanes 3–9 (S-10) are fractions obtained after URP1 chromatography, Lane 10 is the final product obtained after C-18 reverse phase chromatography using the method of this invention. The zeamatin isolated after C-18 reverse phase chromatography appeared homogeneous (95–100% pure) (FIG. 3, Lane 10). FIG. 4 shows the results of Coomassie stained proteins separated by SDS-PAGE for the final product obtained using the prior method (H3-1, Lane 2) and the method of this invention (UPI, Lane 3). In bioautography (FIG. 5) single bands of growth inhibition corresponded to zeamatin isolated from the prior art process (H3-1, Lane 2) and the process of this invention (UPI, Lane 3). In a western blot analysis using zeamatin antibody, a single band corresponding to zeamatin was observed (FIG. 6, Lane 1 is the product obtained from the prior art method).

Example 4 describes the method used to determine the N-terminal sequence of the product isolated by the method of this invention. The N-terminal sequence was consistent with that reported in the literature for zeamatin. (Roberts et al. U.S. Pat. No. 5,559,034, issued Sep. 24, 1996).

Example 5 describes the inhibition assays used to determine the activity of the product obtained by the method of this invention against *Candida albicans* and *Trichophyton mentagrophytes*. In agar diffusion assays, purified zeamatin was active to 0.03 µg against *T. mentagrophytes* and 10 µg against *C. albicans*. These activities are similar to those observed for zeamatin purified using the prior art method.

The method of this invention is not limited to the purification of zeamatin, but rather can be extended to the purification of proteins in general.

The following examples are provided for illustrative purposes only and are not intended to limit the scope of the invention.

EXAMPLES

Example 1

Extraction and purification of high lysine cornmeal (1.0 kg)

The extraction and purification of zeamatin according to the method of this invention is outlined in FIG. 2. Briefly, finely ground cornmeal is extracted with an aqueous phosphate buffer for 24 hours at room temperature. The extract is then clarified by simple filtration and the filtrate is loaded onto a URP1 column and eluted with a step gradient of water/acetonitrile. This steps allows for the elimination of ammonium sulfate precipitation and SEPHADEX™ column used in the prior art method. The URP1 fraction is concentrated and the buffer is exchanged on a Tangential Flow Filter (TFF). The resulting concentrate is then loaded onto a C-18 reverse phase column and the adsorbed proteins eluted with a step gradient of water/acetonitrile.

Extraction.

1.0 kg of high lysine cornmeal, milled to 0.009 inches, was extracted with 2.2 L of aqueous extraction buffer (ABS 10:4.09 g EDTA.2H$_2$O, 7.81 g Na$_2$HPO$_4$, 6.43 g NaCl, 2.2 L H$_2$O) at room temperature for 24 hours under mild agitation. The extraction conditions are summarized in Table 1.

TABLE 1

Extraction Conditions

| Parameter | Value |
| --- | --- |
| Biomass | 1.0 kg |
| Particle size | 0.009 in. |
| Temperature | RT |
| Extraction time | 24 hr |
| Water | 2.2 L |
| NaCl | 6.4284 g |
| Na$_2$HPO$_4$ | 7.8100 g |
| Na$_2$EDTA 2H$_2$O | 4.0942 g |
| pH | 7 |
| Agitation | Mild |
| Impeller | Marine A100 |
| Total Volume | 2.83 L |

Clarification of Extract.

The resulting slurry was clarified by pressure filtration. The well stirred slurry was pumped into a 1.4 L 316 SS pressure filter equipped with Whatman #2 filter paper. The filtration conditions are set forth in Table 2.

TABLE 2

First Filtration

| Parameter | Value |
| --- | --- |
| Slurry Volume | 2.830 mL |
| Density | 1.07 g/L |
| Filter Area | 113 cm$^2$ |
| Pore Size | 8 μm |
| Maximum Pressure | 15 PSI |
| Solids Loading Capacity | 4.0 g/cm$^2$ |
| Slurry Loading Capacity | 11.5 mL/cm$^2$ |
| Cake Thickness | 4.5 cm |
| Filtration Rate | 0.19 mL/min - cm$^2$ |
| Volume of Filtrate | 1.620 L |
| Fluid recovery | 73.6% |

The cake was dewatered by applying 15 psi of compressed air. The yellowish turbid filtrate was then allowed to stand at 4° C. for at least 48 hours. This settling step allows for further clarification of the filtrate as evidenced by the slimy precipitate at the bottom of the vessel. The supernatant was then pressure filtered over Whatman (1 mm pore size) glass fiber filter paper. Precautions were taken to avoid disturbing the precipitate that was left behind and discarded after the second filtration. The data for the second filtration is set forth in Table 3.

TABLE 3

Second Filtration

| Parameter | Value |
| --- | --- |
| Initial Volume | 1.620 L |
| Filter Area | 113 cm$^2$ |
| Pore Size | 1 μm |
| Maximum Pressure | 2 PSI |
| Solids Loading Capacity | NA* |
| Liquid Loading Capacity | NA |
| Filtration Rate | 2.3 mL/min - cm$^2$ |
| Volume of Filtrate | 1.460 L |
| Solid Content | 27.1 g/L |
| Recovery | 90.1% |

*NA: not available

After clarification, about 66% of the 2.2 L of water originally used in the extraction was recovered. The solid content in the clarified extract, named S10 (FIG. 2) was lower than in the prior art method of zeamatin extraction involving centrifugation as shown in FIG. 1 (≅25 g/L). UV-Vis data (not shown) shows the filtrate obtained from the new process exhibited lower absorbance than that of the initial centrate from the prior art procedure ("S10 extract" in FIG. 1) with centrifugation. Both S10 isolated by the prior art procedure or the subject filtration method exhibited the same protein bands when analyzed by SDS-PAGE (data not shown).

URP1 Chromatography.

The S10 filtrate was then loaded onto a URP1 column, previously equilibrated with water. The column medium was AMBERCHROM™ MD-P, an aromatic resin purchased from Toso Haas, Tokyo, Japan (CG161 SD, 35 μm particle size). The column was then washed with 6 column volumes (CVs) of water then eluted with a two step gradient of acetonitrile (ACN)/0.1% aqueous acetic acid. Zeamatin was eluted with 35% ACN in 0.1% aqueous acetic acid. The column was then cleaned with 100% ACN and re-equilibrated with water. Pertinent data on the column is found in Tables 4 and 5.

TABLE 4

Column Conditions.

| Parameter | Value |
| --- | --- |
| Column Geometry | 6.35 × 17.5 cm |
| Resin | URP1 |
| Column Volume (CV) | 550 mL |
| Solid Loading Capacity | 72 g/L |
| Filtrate Loading Capacity | 2655 mL/L of resin |

TABLE 5

Elution Profile of Capture Column.

| Eluent | Volume (mL) | # of CVs | LV (cm/min) | Pressure (PSI) |
| --- | --- | --- | --- | --- |
| Deionized (DI) Water | 3,300 | 6 | 1.6–2.0 | <3 |
| 20% ACN/0.1% aq. AcOH | 3,300 | 6 | 1.6–2.3 | <3 |
| 35% ACN/0.1% aq AcOH | 2,750 | 5 | 2.3–2.6 | 3–4 |
| 100% ACN | 1,000 | 2 | 0.3–0.9 | <3 |

A material balance on the solids was performed to ensure the cleanliness of the column and to avoid resin fouling. It was determined that 60.6% of the solids loaded on the column eluted in the loading solvent, 19.2% of the solids eluted in the water wash and the 20% ACN fraction contained 8.08% of the solids. The fraction containing zeamatin (35% ACN fraction) contained only 4.04% of the solids loaded on the column. The column wash fraction (100% acetonitrile) contained less than 2% of the solids loaded. Recovery of solids was better than 93%, indicating that the solvent profile used to elute the column is efficient in removing solids and cleaning the column. Thus, the possibility of fouling the resin is remote and drastic resin cleaning may be required only after 10 to 20 runs. The data is summarized in Table 6.

TABLE 6

Material Balance on Solids.

| Material | [Solids] mg/mL | Net Solids (g) | % of Loaded Solids |
|---|---|---|---|
| Loading Material | 27.1 | 39.6 | NA |
| Loading Eluent | 16.9 | 24.0 | 60.6 |
| DI wash | 2.3 | 7.6 | 19.2 |
| 20% ACN Eluent | 1.0 | 3.2 | 9.09 |
| 35% ACN Eluent | 0.6 | 1.6 | 4.04 |
| 100% ACN | 0.5 | 0.5 | 1.26 |
| % Recovery | | | 93.2 |

The acetonitrile in each of the fractions from the URP1 column was removed under reduced pressure and gentle heating. The resulting aqueous solutions were lyophilized. The solids were then analyzed for total protein content using the Bradford assay. The results are shown in Table 7.

TABLE 7

Protein Content* in the Capture Column Fractions.

| Fraction | Solids (g) | Total Protein (mg) | % Protein in Solids | % of Total Protein |
|---|---|---|---|---|
| 20% ACN | 3.2 | 192 | 6 | 26.2 |
| 35% ACN | 1.6 | 496 | 31 | 67.7 |
| 100% ACN | 0.5 | 45 | 9 | 6.1 |
| Loading Material | 39.6 | 733 | 1.85 | — |

*The above data is from one single run.

Based on these results, the amount protein in the filtrate that was retained by URP1 resin is 502 mg/L (1.85% based on the solids loaded). It should be noted that these protein contents are limited to the protein retained by URP1 resin, since the protein content in the loading eluent or DI water wash (see Table 6) are not known and/or included. A better material balance could be achieved if the protein content in the S10 extract was known. The bulk (about ⅔) of the proteins retained by the resin elute in the zeamatin containing fraction (35% ACN).

HPLC analysis of the fractions (data not shown) showed that the bulk of zeamatin is in the 35% ACN fraction, and that negligible amounts are found in 20% or the 100% ACN fractions.

The zeamatin in the 35% acetonitrile fraction (URP1 fraction in FIG. 2) was removed under reduced pressure using a rotatory evaporator, the resulting aqueous solution was then lyophilized.
C-18 Chromatography.

The solids from the 35% ACN best pool were dissolved in deionized water to a final concentration of 15 mg/mL and then filtered on 0.45 μm filter. The pH of the solution was determined calorimetrically (pH strip) and found to be between 4 and 5. A 200 μL aliquot was loaded onto a C-18 (ODS-AQ 15 μm particle size, 200 Å pore size; YMC Inc.) column previously equilibrated with 5% ACN in 0.1% aqueous trifluoroacetic acid (TFA). The column was eluted with a step gradient of ACN in 0.1% aqueous TFA, and the elution was monitored at 214 nm. Details about this column are found in Table 8.

TABLE 8

Reverse Phase Column Conditions.

| % ACN in 0.1% Aqueous TFA | Flow Rate (mL/min) | Pressure (PSI) | Number of CVs |
|---|---|---|---|
| 5 | 3 | 1050 | 1 |
| 37 | 3 | 1050 | 5 |
| 39 | 3 | 1050 | 2 |
| 39→100 | 3 | 1050 | 3 |
| 100 | 3 | 1050 | 2 |
| 100→5 | 3 | 1050 | 5 |

Zeamatin elutes in the 39% ACN fraction (retention time≅38.5 minutes). Zeamatin containing fractions from three different runs were combined (URP13 Best Pool in FIG. 2; 21 mL) and concentrated on a rotary evaporator at a temperature not exceeding 30° C. to 5 mL. The concentrate was then dialyzed against 4 volumes of a 20 mM NaCl solution using 5,000 Dalton nominal molecular weight cut-off Amicon Ultrafree-0.5 centrifugal filtration tubes. The final solution (5 mL and pH 6) was then lyophilized. The white solids were then assayed for purity using SDS polyacrylamide gel electrophoresis (data not shown). The results showed that the zeamatin was purified to greater than 95% purity.

Example 2

Extraction and purification of high lysine cornmeal (5 kg)

The extraction and purification of zeamatin according to the method of this invention is outlined in FIG. 2. In this example the process is carried out on a much larger scale (5 kg) and the C-18 fraction containing zeamatin is concentrated and dialyzed to yield zeamatin purified to homogeneity.
Extraction.

High lysine cornmeal (5.0 kg, 60 mesh (Arrowhead Mills)) was added under vigorous agitation to a 20 L container equipped with a mechanical agitator containing 11.0 L of phosphate buffer (25 mM $Na_2HPO_4$, 50 mM NaCl, 5 mM EDTA, disodium salt, pH 7). The thick slurry was agitated for 24 hours at room temperature. The mechanical stirrer consisted of a Cole-Parmer motor Model 4554-20 and a stainless steel A100 axial flow impeller. The impeller was off-centered and angled by approximately 15° to simulate a baffled extraction vessel.
Clarification of Extract.

The extract can be clarified using a variety of solid/liquid separation techniques, including but not limited to centrifugation, vacuum filtration or pressure filtration. In small scale experiments, the suspension was centrifuged for 20 minutes at 4° C. and 10,000 g.

The resulting slurry was also clarified by a tandem or single pressure filtration, which is preferable on a large scale. The slurry was pumped into a 10"×12" stainless steel pressure filter equipped with 40 μm filter paper (VWR Scientific Products, Grade 417) using a peristaltic pump (Masterflex Model) equipped with an Easy-Load pump head (Masterflex Model) and L/S 24 PharMed tubing (Masterflex). The clarified extract is hereafter referred to as the "S10 extract."

URP1 Chromatography.

The S10 extract was loaded directly onto a URP1 column (flanged glass column 10 cm id×60 cm) previously equilibrated with water using a Teflon diaphragm pump (Masterflex Model). The column was then washed with about 3 CVs (column volumes) of water and 2.5 CVs of 0.1% acetic acid in 15% acetonitrile/water. Zeamatin was eluted with 2.5 CVs of 0.1% acetic acid in 40% acetonitrile/water. Column elution was monitored with an online system consisting of a Rainin UV-C Dynamax UV detector set at 214 nm and Hewlett-Packard Model 3395 integrator.

The zeamatin containing fraction (URP1 fraction) was neutralized to pH 7 by the addition of aqueous $NaHCO_3$ (1 M solution). The neutralized solution was then concentrated to about 1 L on a Millipore stainless steel Pellicon Tangential Flow Filter equipped with a 5.36 $ft^2$ 5 kDa Pellicon-2 composite regenerated cellulose membrane. The concentrate was then dialyzed against 6 volumes of NaCl (20 mM solution) to reduce the acetonitrile content to under 0.6% by volume. The dialyzed URP1 fraction (DURP1) was stored at 30° C.

C-18 Chromatography.

The dialyzed URP 1 fraction containing zeamatin was loaded onto a C-18 (ODS-AQS 10/20 200 AS, YMC inc.) column (flanged stainless steel 10 cm id×10 cm) previously equilibrated with 5% acetonitrile/water containing 0.1% TFA. The solvents were pumped onto the column using a Rainin Dynamax Model SD-1 solvent delivery system. The column was eluted with a multi-step gradient of 0.1% TFA in acetonitrile/water as set forth in Table 9 below.

Column elution was monitored with an online system consisting of a Rainin UV-C Dynamax UV detector set at 214 nm and Hewlett-Packard Model 3395 integrator. Zeamatin eluted as a single pool in the 37% acetonitrile/water.

The fraction containing the zeamatin was neutralized to pH 7 with aqueous $NaHCO_3$ (1 M) and concentrated to about 1 L. The concentrate was then dialyzed six times against an equal volume of aqueous NaCl (20 mM) to reduce the acetonitrile to 0.5% and the trifluoroacetate to 0.0015%. The concentrate containing zeamatin purified to homogeneity, was then stored at −70° C.

TABLE 9

Elution Parameters for the C-18 Column

| Mobile Phase | Volume (L) | Flow Rate (mL/min) | Max. Pressure psi |
|---|---|---|---|
| Load Material | 0.8 | 150 | 90 |
| 5% ACN/water containing 0.1% TFA | 3.0 | 250 | 100 |
| 20% ACN/water containing 0.1% TFA | 8.0 | 250 | 160 |
| 30% ACN/water containing 0.1% TFA | 8.0 | 250 | 155 |
| 33% ACN/water containing 0.1% TFA | 8.0 | 250 | 160 |
| 35% ACN/water containing 0.1% TFA | 8.0 | 250 | 150 |
| 37% ACN/water containing 0.1% TFA | 10.0 | 250 | 150 |
| 55% ACN/water containing 0.1% TFA | 8.0 | 250 | 140 |

Example 3

Analysis of zeamatin

SDS/PAGE Analysis. SDS-PAGE was performed following the method of Sambrook el al. using 12% polyacrylamide gel (100×140×0.75 mm) with a 5% polyacrylamide stacking gel (20×140×0.75 mm). (Sambrook et al. (1989) Molecular Cloning A Laboratory Manual, $2^{nd}$ edition, Cold Spring Harbor Laboratory Press, NY, which is incorporated herein by reference in its entirety). Samples were boiled for 4 minutes in Laemmli sample buffer prior to loading. (Laemmli (1970) Nature 227:680–685, which is incorporated herein by reference in its entirety). Gels were run for 3.5 to 4 hours at 250 V until the dye front reached the bottom of the gel. The protein(s) on the gels were visualized using a silver stain kit following manufacturer's instructions (Boehringer Mannheim) or by Coomassie stain (Vigers and Selitrennikoff (1991) Mol. Plant Microbe Interac. 4:315–323 30). The percentage of zeamatin in each lane was determined using 1D-multi densitometry (IS-1000 v. 1.97 software Alpha-innotech Corporation, San Leandro, Calif.). Protein determination for samples analyzed for zeamatin purification was done using the BCA method (Pierce, Rockford, Ill.)

Western Blot. Samples to be tested were separated by SDS/PAGE as described above. Gels were blotted for 20 minutes (10V) onto BioTrace NT nitrocellulose (Gelman Sciences) using a semi dry blotter (Bio-Rad) with transfer buffer (48 mM Tris, pH 8.5, 39 mM glycine, 0.037% [w/v] SDS, and 20% [v/v] methanol). Blots were blocked for 1 hour at room temperature in Tris-buffered saline (TBS, 50 mM Tris, 8.5% [w/v] NaCl, pH 7.4) containing 0.1% Tween-20 and 5% [w/v] nonfat milk powder (TBS-T). Primary antiserum (1:1000) was added to the blocking buffer and incubated overnight at room temperature. The blot was then washed three times briefly and 4 times for 5 minutes each with TBS-T. The secondary peroxidase goat-anti-rabbit antibody (Boehringer Mannheim Biochemical, Indianapolis, Ind.) was added and incubated for 1 hour followed by washes as described above. Bound HRP was measured by incubation of the blot in HRP chemiluminescent substrate (ECL™; Amersham) and visualized by autoradiography.

Bioautography. SDS/PAGE analysis was performed as described above, except samples were boiled for 4 minutes in sample buffer (15% [w/v] sucrose, 2.5% [w/v] SDS, 125 mM Tris, pH 6.8). The resulting gels were then incubated with shaking in 250 mL of 1% (v/v) Triton X-100 in water for 20 minutes at room temperature. After a brief washing in water, the gels were incubated in 100 mL of 4% (w/v) carrot extract and gently shaken for 30 minutes at room temperature. Finally, the gels were placed in 150 mm diameter petri dishes and 30 mL of warm agar (1.5% [w/v] agar, 4% [w/v] carrot extract, 0.2 mg/mL of nikkomycin Z and $2.5 \times 10^5$ C. albicans cells per milliliter final concentration) was poured over the gels and allowed to solidify. The C. albicans strain B366 (ATCC 56884) was used for this assay was described previously by Vigers and Selitrennikoff (1991) Mol. Plant Microbe Interac. 4:315–323 30, which is incorporated herein by reference in its entirety. After overnight incubation at 37° C., the position of anti-candidal activity on the gel was detected as a clear zone of growth inhibition against a background of candidal growth.

Example 4

N-terminal sequence analysis

SDS/PAGE analysis was performed as described in Example 3, using a Bio-Rad MiniProtean II apparatus (Bio-Rad; Hercules, Calif.) to perform the gel electrophoresis. Zeamatin (200 pmol) was loaded per well in triplicate. The resulting gel was transferred onto a IMMUN-BLOT™ PVDF blotting membrane (0.2 μm) (Bio-Rad; Hercules, Calif.) using a semi dry blotter (Gelman Sciences) and transfer buffer as in Example 2 for the western blot procedure. The blot was rinsed briefly with water and stained with Coomassie Stain (0.25% Coomassie Brilliant Blue R250, 45% methanol) for 10 minutes. The blot was destained for 5 days with 45% methanol and then air-dried. Purified zeamatin was sequenced from the blot at the protein sequencing core facility at Colorado State University (Fort Collins, Colo.). The sequence was consistent with the published N-terminal sequence of zeamatin. (Roberts et al. U.S. Pat. No. 5,559,034, issued Sep. 24,1996).

Example 5

Inhibition assays

*Candida albicans.* Growth inhibition of *C. albicans* by zeamatin was determined as described by Roberts and Selitrennikoff (1990) J. Gen. Microbiol. 136:771–1778, which is incorporated herein by reference in its entirety). Briefly, agar assay plates were prepared by autoclaving 4% carrot extract and 1.5% washed agar, cooling to ~50° C. and adding *C. albicans* (B366; ATCC 56844) to a final concentration of 2.5 $10^5$ cells per milliliter. 30 mL aliquots of this warm medium were added to 150 mm diameter petri dishes and allowed to solidify before placing test samples onto the surface of the agar. 25 μL of various concentrations of sample were added to the surface, dried and the plates were incubated overnight at 37° C. The plates were examined for zones of growth inhibition around each spot. The lowest concentration of protein that produced a detectable zone of inhibition was considered the minimum inhibitory dose (MID) and is expressed as micrograms of protein per spot. In plates in which nikkomycin was present, nikkomycin Z (Calbiochem Corporation, San Diego, Calif.) was added to the agar at 45° C. to give a final concentration of 0.2 mg/mL.

*Trichophyton mentagrophytes.* Growth inhibition of the *T. mentagrophytes* by zeamatin was determined using dermatophyte test medium (Becton Dickinson). Briefly, agar assay plates were prepared by autoclaving 4.1% dermatophyte test medium, cooling to ~50° C. and adding *T. mentagrophtyes* (ATCC 18751) to a final concentration of $5 \times 10^5$ cells per milliliter. 30 mL aliquots of this warm medium were added to 150 mm diameter petri dishes and allowed to solidify before placing test samples on to the surface of the agar. 25 μL of various concentrations of sample was added to the surface, dried and the plates were incubated for 36–48 hours at 35° C. Plates were examined for zones of growth inhibition around each spot. The MID was determined as described above.

What is claimed is:

1. A method for the purification of zeamatin from corn comprising,
    (a) extracting corn with an aqueous buffer to yield an initial suspension;
    (b) filtering said initial suspension to yield a filtrate;
    (c) fractionating said filtrate using capture chromatography, and collecting one or more initial eluted fractions containing zeamatin;
    (d) further fractionating said initial fractions containing zeamatin using reverse phase chromatography, and collecting one or more further eluted fractions containing zeamatin; and
    (e) concentrating said further fractions containing zeamatin;
    wherein said method does not include ammonium sulfate precipitation, followed by centrifugation.

2. The method of claim 1 wherein said initial eluted fractions and said further eluted fractions containing zeamatin are identified by high pressure liquid chromatography.

3. The method of claim 1 wherein said initial eluted fractions and said further eluted fractions containing zeamatin are identified by sodium dodecyl sulfate polyacrylamide gel electrophoresis (SDS-PAGE).

4. The method of claim 1 wherein said capture chromatography is performed with an organic solvent.

5. The method of claim 1 wherein said capture chromatography is performed with a solvent comprising acetonitrile (ACN) and 0.1% aqueous trifluoroacetic acid.

6. The method of claim 1 wherein said reverse phase chromatography is performed with an organic solvent.

7. The method of claim 1 wherein said reverse phase chromatography is performed with a solvent comprising acetonitrile (ACN) and 0.1% aqueous trifluoroacetic acid (TFA).

8. The method of claim 1 wherein step (e) is performed using evaporation and lyophilization.

9. The method of claim 1 further comprising a diafiltration step between steps (b) and (c).

10. The method of claim 1 further comprising a diafiltration step between steps (c) and (d).

11. The method of claim 1 wherein step (e) is performed using a diafiltration step.

12. The method of claims 9, 10, or 11 wherein said diafiltration step is performed using a 5 kDa nominal molecular weight cutoff membrane.

13. The method of claim 1 further comprising a cation exchange chromatography step between steps (c) and (d).

14. The method of claim 13 wherein the cation exchange chromatography step is performed using a carboxymethyl cation exchange resin.

15. The method of claim 1 wherein the capture chromatography is performed using an aromatic resin.

16. The method of claim 15 wherein said aromatic resin is selected from the group consisting of CG 161, CG 71 or CG 3000.

17. The method of claim 1 wherein the reverse chromatography is performed using a C-18 resin.

18. The method of claim 17 wherein said C-18 resin has a hydrophilic end cap.

19. A method for the capture and purification of proteins comprising,
    (a) preparing a protein extract from a plant or animal source;
    (b) fractionating said extract using capture chromatography, and collecting one or more initial eluted fractions containing said protein; and
    (c) further fractionating said initial fractions containing said protein using reverse phase chromatography, and collecting one or more further eluted fractions containing said protein;
    wherein said method does not include ammonium sulfate precipitation, followed by centrifugation.

* * * * *